United States Patent [19]
Cook et al.

[11] Patent Number: 4,551,143
[45] Date of Patent: * Nov. 5, 1985

[54] NONWOVEN FIBROUS PRODUCT AND METHOD OF MAKING SAME

[75] Inventors: John R. Cook, Downers Grove; William A. James, Tinley Park, both of Ill.

[73] Assignee: Johnson & Johnson Baby Products Company, New Brunswick, N.J.

[*] Notice: The portion of the term of this patent subsequent to Jul. 5, 2000 has been disclaimed.

[21] Appl. No.: 622,399

[22] Filed: Jun. 21, 1984

Related U.S. Application Data

[60] Continuation of Ser. No. 366,509, Apr. 8, 1982, abandoned, which is a division of Ser. No. 194,511, Oct. 6, 1980, Pat. No. 4,391,869.

[51] Int. Cl.$^4$ .............................................. A61F 13/16
[52] U.S. Cl. ..................................... 604/371; 604/367
[58] Field of Search ............... 604/370, 371, 372, 365, 604/366, 367

[56] References Cited

U.S. PATENT DOCUMENTS

| | | | |
|---|---|---|---|
| Re. 30,061 | 7/1979 | Shepherd | 156/78 |
| 2,982,682 | 5/1961 | Matlin et al. | 154/101 |
| 3,007,840 | 11/1961 | Wilcox | 162/101 |
| 3,515,634 | 6/1970 | Sommer et al. | 162/146 |
| 3,589,956 | 6/1971 | Kranz et al. | 156/62.4 |
| 3,676,245 | 7/1972 | Helmut et al. | 156/181 |
| 3,755,036 | 8/1973 | Paquette et al. | 156/180 |
| 3,987,792 | 10/1976 | Hernandez et al. | 604/365 |
| 4,010,752 | 3/1977 | Denny | 604/370 |
| 4,041,203 | 8/1977 | Brock et al. | 428/157 |
| 4,044,768 | 8/1977 | Mesek et al. | 604/365 |
| 4,081,582 | 3/1978 | Butterworth et al. | 428/284 |
| 4,082,886 | 4/1978 | Butterworth et al. | 428/284 |
| 4,159,355 | 6/1979 | Kaufman | 427/209 |
| 4,391,869 | 7/1983 | Cook et al. | 604/370 |

Primary Examiner—C. Fred Rosenbaum
Assistant Examiner—Sherri E. Vinyard
Attorney, Agent, or Firm—Martha A. Michaels

[57] ABSTRACT

Nonwoven, air-laid fabrics formed predominantly of textile length, synthetic, resilient fibers of staple length, the fabric being resin-bonded and having a density less than about 0.06 gm/cc at 0.16 lb/sq. in. load and a weight less than 3 oz/sq. yd. The fabric is resin-bonded using a bonding solution providing less than 180% solution pickup and more than 15% dry solids add-on. The fabric is used as a facing or covering for disposable diapers, sanitary napkins, incontinent pads, tampons and the like.

6 Claims, 9 Drawing Figures

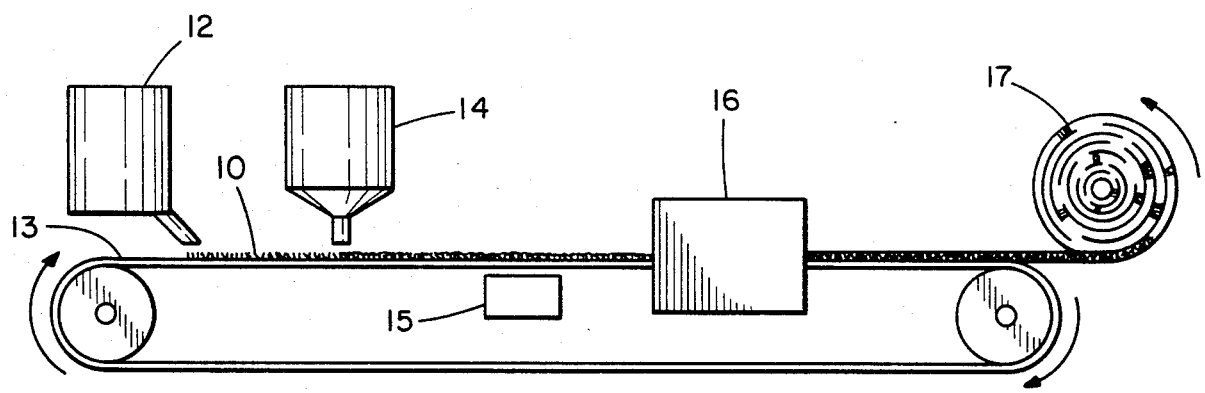
FIG.1
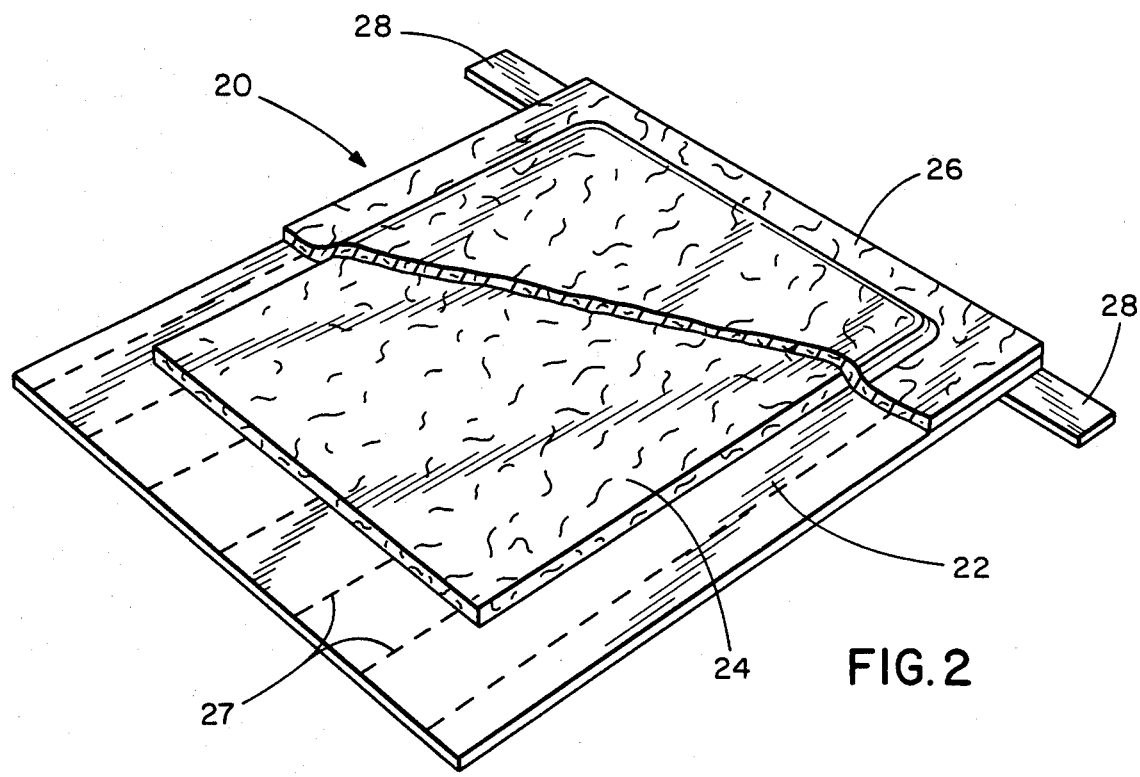
FIG.2
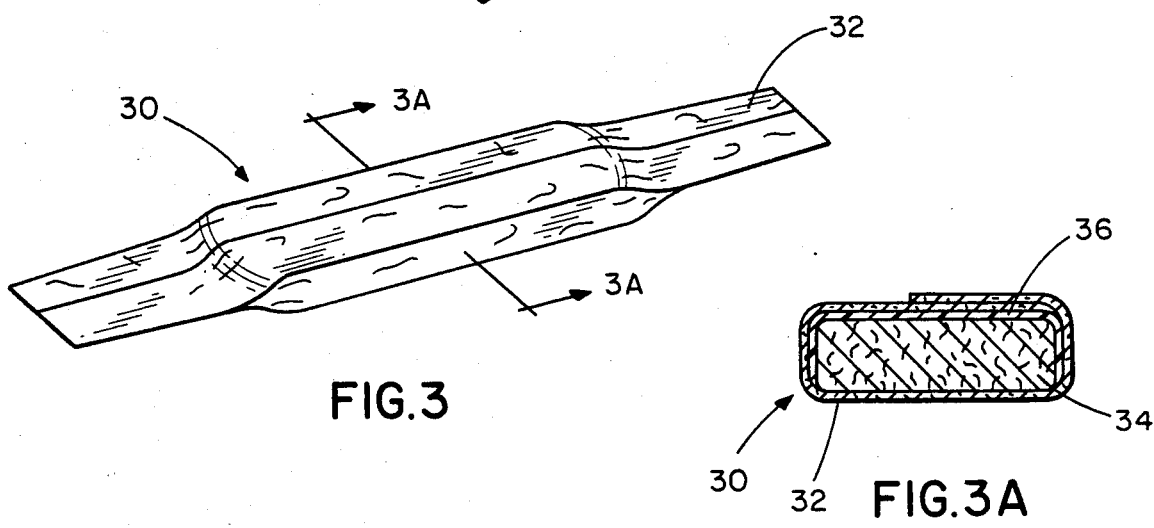
FIG.3
FIG.3A

NONWOVEN FIBROUS PRODUCT AND METHOD OF MAKING SAME

This application is a continuation of application Ser. No. 366,509, filed Apr. 8, 1982, now abandoned, which is a division of application Ser. No. 194,511, filed Oct. 6, 1980, now U.S. Pat. No. 4,391,869.

BACKGROUND OF THE INVENTION

This present invention relates to nonwoven, air-laid fabrics formed predominantly of textile length synthetic fibers, the method of making the same, and products formed therefrom. The present invention also relates to disposable absorbent articles such as disposable diapers, incontinent pads, sanitary napkins, nursing pads, and the like, utilizing the fibrous web produced.

Despite the advanced state of the art of liquid-pervious, resin-bonded, nonwoven fabrics, a satisfactory method of producing such a fabric having very low density and high loft, and which is liquid pervious, has not been developed previously.

Disposable absorbent articles such as disposable diapers, provide substantial advantages and convenience over diapers that have to be laundered and reused, particularly when the diapers are used away from home. In recent years, many different disposable diapers have been proposed and some have been successful in the marketplace. However, even the successful diapers may be inadequate in some of the functioning properties, and their commercial success has come, at least in part, because consumers have been willing to accept inadequate performance as part of the price for convenience.

One design criterion which has not heretofore been met adequately is keeping moisture away from the surface of the diaper which comes into contact with the infant's skin. The portion of the diaper nearest the infant's skin is generally identified as the facing layer. Ideally, the facing layer should permit a void of urine to rapidly permeate the layer, but after permeation of the layer, the facing should not permit the wetness to come back through the facing to the infant's skin.

One disposable diaper representing a significant advance in the art, is a multi-layer diaper comprising, in order, a fibrous facing layer which is to be brought into contact with the infant's skin; a layer of highly porous, loosely compacted cellulosic batt; a paper-like densified, highly compacted batt; and a moisture-impervious backing sheet adhered to the densified layer at the interface therebetween. The facing layer is of porous construction and its fibers have less wettability for water than the fibers of the loosely compacted batt, resulting in a tendency for liquid to flow from the facing layer into the batt. The densified fibrous layer has a smaller average pore size than the loosely compacted batt, resulting in a tendency for liquid to flow preferentially from the batt into the underlying densified layer rather than to other areas of the batt, thus tending to restrict wetting in the batt to an area of moderate size. Liquid flowing into the densified layer tends to spread laterally because of the wicking action of the densified layer and liquid which might pass through the densified layer during discharge is held back by the impervious backing sheet usually for a sufficient time to permit absorption to take place. Liquid in excess of the absorptive capacity of the densified layer is forced back by the impervious layer into the dry portion of the loosely compacted batt, thus utilizing the additional absorptive capacity therein.

However, while the diaper structure described above presents a significant advance in the art, during heavy periods of discharge, after the densified layer and integral loosely compacted batt become wetted to a high level, there is a tendency to wet back into the facing layer. When the facing layer becomes wet, the urine wets the infant's skin and discomfort or irritation can take place. It has been found that a low density, resin-bonded, nonwoven fabric of resilient synthetic fibers permits the liquid to pass through the fabric rapidly, but the fabric is not readily rewetted.

Nonwoven materials are structures which, in general, consist of an assemblage or web of fibers, joined randomly or systematically by mechanical, chemical or other means. These materials are well known in the art, having gained considerable prominence within the last twenty years or so in the consumer market, industrial commercial market, and the hospital field.

There are two basic techniques for forming individual fibers into webs or sheets to provide nonwoven materials such as nonwoven fabrics. One method is the wet laying of fibers on a screen or wire to form paper or paper-like sheets. The other method which is of particular interest herein is laying the fibers in a dry condition either by carding or air-blowing against a foraminous support. Frequently a binder is added to assist in holding the fibers in place. The latter dry-formed webs are generally of a lesser density with a high loft and are more liquid pervious than the paper-like sheets.

Generally, when a fibrous web is dry laid, it is in an unstabilized state, for instance, wherein the fibers are carried in an air stream and deposited on a foraminous belt or cylinder. Thereafter, the web can be bonded by impregnating the same with a binder throughout. The weight of the binder material, as well as the application technique, tend to compact the web somewhat, thus increasing the web density and reducing its bulk.

SUMMARY OF THE INVENTION

The nonwoven fabric provided herein represents a significant improvement over fabrics known heretofore because of its low density, high loft, resiliency and liquid permeability. The fabric is made from resilient, synthetic, staple fibers. When the fabric of the present invention is used as a facing layer in a disposable diaper product, a void of urine is easily passed therethrough, but upon subsequent voids to the diaper, rewetting of the facing layer is substantially less than known heretofore.

To achieve this important and desirable result, the non-woven fabric of the present invention is a resin-bonded, low density, high loft fabric made from synthetic, staple resilient fibers. The fabric has a density less than about 0.06 gm/cc at 0.16 lb/sq.in. load and has a weight less than about 3 oz/sq.yd. The fabric is made by providing a nonwoven web of discrete, resilient, synthetic staple fibers, such as polyester fibers; impregnating the web with an aqueous resin binder capable of stabilizing the fibers, the amount of the aqueous binder being less than the amount necessary to provide a solution pickup of 180% and sufficient to provide a dry solids add-on of at least 15%; and drying the web.

BRIEF DESCRIPTION OF THE DRAWING

FIG. 1 is a schematic view illustrating one method for the preparation of the fabric of the present invention;

FIG. 2 is a perspective view of one embodiment of the present invention in the form of a diaper with a section broken away for clarity;

FIG. 3 is a perspective view of an embodiment of the present invention in the form of a sanitary napkin;

FIG. 3A is a cross-sectional view of the sanitary napkin of FIG. 3 taken along lines 3A—3A;

DETAILED DESCRIPTION OF THE INVENTION

Figure 4:
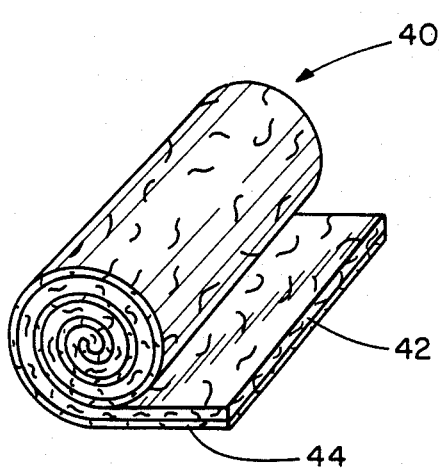
FIG. 4 is a perspective view of a partially rolled blank for compressing into a finished catamenial tampon embodying the invention.

The fabrics of the present invention have a fiber content which is predominantly long fibers. The term "long fibers" as used herein refers to textile fibers having a length greater than about $\frac{1}{4}''$ and the fibers are non-cellulosic and of synthetic origin. Generally, the fibers are between $\frac{1}{2}$ and $2\frac{1}{2}$ inches in length. In the preferred form of the invention, the long fibers are preferably from about 1 to 2 inches in length.

The fabrics of the present invention have fabric weights in the range of about 0.5 to about 3 oz/sq.yd., preferably from about 0.5 to about 2 oz/sq.yd., a density of less than 0.06 gm/cc at 0.16 lb/sq.in. load, preferably in the range from about 0.02 to about 0.05 gm/cc. A typical fabric having a weight of about 0.7 oz/sq.yd. and a density of about 0.03 gm/cc will have a machine direction dry tensile strength of at least 1 and generally between about 1.5 and 2.0 lb/in. of width. For the same fabric, the cross direction dry tensile strength would be at least 0.6 and generally from about 1.0 to about 1.5 lb/in. of width. The fabrics have exceptionally high loft while retaining unusually good elongation in the machine direction, softness and drape characteristics when compared with prior products made from staple synthetic fibers.

The fabrics are prepared by first forming a nonwoven web of dry fibers. The fibers are synthetic, resilient, staple fibers such as polyester fibers. In the preferred method of manufacture, the web is impregnated with a binder by flowing a solution or dispersion of the binder through the web. The impregnated web is then subjected to suction to remove excess binder and assure uniform distribution of binder throughout the fibrous web. This impregnation by the binder, when followed by suction, is hereinafter referred to as "suction-bonding." It has been discovered that unusually high loft and low density is obtained in the final product when the suction bonding process is controlled, so as to provide less than about 180% solution pickup by the web during bonding. The term "solution pickup" (SPU) refers to the amount of weight increase of the web when containing the aqueous binder prior to drying, in proportion to the original weight of the web before application of the aqueous binder. Thus, a solution pickup of 180% represents a weight gain of 1.8 in proportion to a web initially weighing 1.

In the present invention, though the solution pickup is less than conventional processes, it is still necessary to have sufficient binder solids content to promote adequate bonding to form the desirable fabric. In the present instance, it is desirable to have a dry solids add-on value between about 15% and about 70%. The term "dry solids add-on" (DSAO) represents the weight of the binder present in the web after drying has taken place expressed in weight percent of the web on an unbonded basis. Preferably the dry solids add-on is from about 30% to about 50%. The SPU level is less than 180% but more than 40%, preferably less than 140% and most preferably in the range from about 80% to about 120%. The web so formed is then dried and heated to cure the binder. This can be done simultaneously by passing the web over heated cans or by placing the web into a heated drying oven whereby the temperature of the fabric reaches at least about 285° F. or higher wherein the web is dried and the binder cured. The preferred binders are what is known as resin binders and are of the self-curing, acrylic, latex family, the urethane family, or other binders commonly used to bond a nonwoven fabric.

The present invention has special advantages in the manufacture of lightweight, low density, lofty and soft fabrics. The especially useful range of fabric densities in accordance with the invention is from about 0.02 to about 0.04 gm/cc and having a loft of from about 50 mils to about 25 mils at a weight of about 0.8 oz/sq.yd. measured at a load of about 0.16 lb/sq.in. In spite of the exceedingly high loft of the fabric, the fabric has good tensile strength in both machine and cross directions.

Fibers suitable for use in the present invention are resilient, synthetic, staple fibers which generally are hydrophobic. Particularly suitable are the softer fibers such as polypropylene, polyethylene, nylon, acrylic, polyester and the like. Most satisfactory fabrics are made entirely from the non-cellulosic synthetic staple fibers, however, minor proportions up to about 25% of short fibers may be added. Typical short fibers are wood pulp, cotton linters or the like where the fiber lengths are less than about $\frac{1}{4}''$.

Bonding techniques other than suction bonding may be used wherein an aqueous binder can be applied and in the process will substantially permeate the web. Typical of such bonding processes are spray bonding and foam bonding. Spray bonding involves spraying a binder onto the web, generally applying some suction, and then passing it into a drying stage. In the instance of foam bonding, foam is applied to one or more surfaces of the web and after the foam has penetrated either by lapse of time or by application of suction, the web is dried and the binder is cured. Print bonding is also satisfactory, however, in the instance of print bonding, some loft may be lost due to the pressures involved in a print bonding technique.

The preparation of the nonwoven fabric in accordance with the present invention is illustrated schematically. For example, in FIG. 1, a web 10 of long fibers 11 is deposited from fiber-laying equipment 12 onto a foraminous moving screen or belt 13. The fiber-laying equipment 12 is preferably of the air deposition type such as a dual rotor. A typical nonwoven web, which is air laid by a dual rotor, is shown in U.S. Pat. No. 4,018,646 to Ruffo et al. The low density fiber web 10 is moved by a belt 13 below a screen containing a Weir box 14 of binder in solution or aqueous dispersion form. The binder fluid flows from the Weir box 14 onto the web 10 in quantities substantially in excess of the ultimate amount to be deposited on the fibers, and impregnates the web. The web 10 immediately after impregnation with the binder solution, passes over a suction box 15 where excess binder is removed. The impregnated web 10 is conveyed by belt 13 through a dryer 16. The fabric is then removed from belt 13 and collected for example on fabric roll 17. It is desirable, when attaining a lofty and soft character to the fabric, that the application, removal and drying of the binder be done without substantial compression of the fabric.

The amount of binder employed will depend on the type of bonding technique used and on the type and quality of product desired. The binder generally is present in an amount of at least about 15% by weight dry basis, but not more than 70% based on the weight of the unbonded web. Amounts substantially above 40% generally tend to produce a stiffer fabric and the fabric has a harsher feel.

The particular type of resin binder used may be selected from a large group of binders now known in the industry for such purposes. Water-insoluble or water-insensitive binders such a melamine-formaldehyde, urea-formaldehyde, or the acrylic resins, particularly the self cross-linging acrylic ester resins, are preferred as they are capable of resisting a subsequent aqueous rearranging treatment. Other binders, however, are also satisfactory and include polyvinyl acetate, polyvinyl chloride, copolymers thereof, polymethyl methacrylate, polyvinyl butyral and the like.

Following bonding, the nonwoven webs may be treated according to conventional procedures for any further desired purpose. For instance, the web or fabric may be treated with a surfactant to enhance liquid permeability. In addition, the web might be treated with a repellent or other coating according to conventional techniques or be bonded to a substrate to provide a laminate.

The products provided by the present invention find use in various fields. These nonwoven webs have a greater utility because of their very high loft while still possessing adequate tensile strength and excellent liquid permeability. Typical uses of the products include facings or coverings for absorbent structures such as disposable diapers, sanitary napkins, incontinent pads, tampons and the like.

Referring now to FIG. 2, a disposable diaper 20 is provided. A moisture-impermeable backing sheet 22 provides the exterior of the diaper product. An absorbent batt 24 is placed in superposed position to the backing sheet. The absorbent batt is covered with the facing 26. The facing is the nonwoven product of the present invention. The diaper 20 is laminated by use of glue lines 27 and is affixed securely about the waist of the wearer by use of tape tabs 28.

FIGS. 3 and 3A depict a typical sanitary napkin 30. The napkin contains an absorbent core 34 partially encompassed by a moisture-impermeable barrier 36. The absorbent core and the barrier are wrapped by the cover 32. The cover is the nonwoven product of the present invention.

Figure 5:
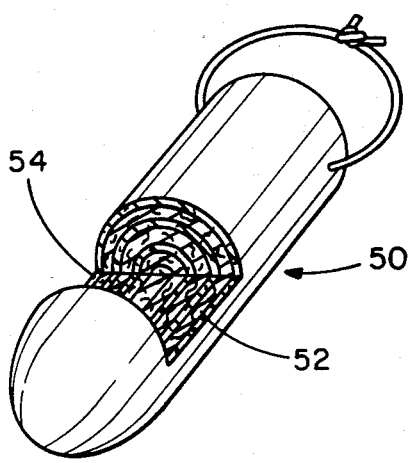
FIG. 5 is a perspective view of a finished tampon made from the blank of FIG. 4, a portion thereof being broken away to show interior detail.

FIG. 4 is a tampon blank 40 which when compressed forms the tampon 50 depicted in FIG. 5.

An elongated pad 42 of absorbent material having generally a rectangular shape is superimposed on a nonwoven fabric 44 of substantially the same shape and size. The pad 42 and fabric 44 are formed into a cylinder by rolling from one end to the other in a direction parallel to the longitudinal sides of the pad. FIG. 5 illustrates the shaped tampon 50 prepared from the cylinder blank. The fragmentary view shows the absorbent pad 52 and the nonwoven fabric 54. It should be noted that the nonwoven fabric 54 of the present invention provides the exterior cover of the tampon 50.

The process of the present invention has many advantageous features over prior art bonding techniques. One advantage is obtaining a random nonwoven web having machine direction and cross direction strengths approaching a ratio of 1:1, respectively, while at the same time having excellent appearance and good hand and drape. Still further, the advantages include a high degree of uniformity in web structure and a decrease in cost of production resulting from less moisture to be removed upon drying. In addition, a web of considerable loft is produced having less fiber content but still having adequate tensile strength and functionality.

The nonwoven product has substantial abrasion resistance and cohesive strength as well as nonabsorption characteristics. The nonwoven product of the present invention is particularly suitable for use as a facing in a disposable diaper product. Typically, a disposable diaper consists of a backing sheet, an absorbent batt and a facing. Generally, the facing and the backing extend beyond the absorbent batt and are adhered one to the other so as to provide an integral product. In addition to the high loft and excellent softness of the web of the present invention, the web when used as a facing on a diaper does not permit ready transfer of liquid from a highly wetted absorbent batt back through the facing to the infant's skin.

The preparation of fabrics of the present invention are further illustrated by the following examples. Examples are given for the purpose of illustration only and the invention is not limited thereto.

EXAMPLE 1

Polyester fibers of staple fiber length are air laid by a dual rotor web-forming device to obtain a web 45" in width weighing about 0.5 oz/sq.yd. The web is subjected to suction bonding in a conventional manner using an aqueous resin binder solution containing about 22% solids. The adhesive is generally applied to the upper surface of the web while suction is applied on the opposite surface. The adhesive is applied so as to provide solution pickup (SPU) of about 135% and dry solids add-on (DSAO) of about 30%.

The samples are dried on one stack of steam cans at 225° F., followed by two stacks of steam cans at 300° F. The speed of the web is 52 feet per minute.

Fabric samples A,B, and C of the present invention and several prior art samples, P-T, are tested for dry surface wetness as well as thickness, weight and density and are set forth in Table 1.

The thickness is measured in mils (thousandths of an inch) and the weight in ounces per square yard. The density is in grams per cubic centimeter having a load of 0.16 pounds per square inch.

TABLE 1

| Sample No. | Thickness Mils @ 0.16 oz/sq. in. load | Weight oz/yd² | Density gm/cc @ 0.16 oz/sq. in. load |
|---|---|---|---|
| A | 17.5 | 0.77 | 0.059 |
| B | 23.7 | 0.73 | 0.041 |
| C | 59.9 | 0.87 | 0.019 |
| Prior Art | | | |
| P | 6.7 | 0.76 | 0.152 |
| Q | 8.5 | 0.76 | 0.119 |
| R | 8.0 | 0.69 | 0.116 |
| S | 11.0 | 0.76 | 0.092 |
| T | 14.8 | 0.78 | 0.071 |

The different thicknesses and densities in Samples A, B and C can be obtained by applying pressure and slight heat to a low density, high loft fabric such as Sample C.

Figure 6:
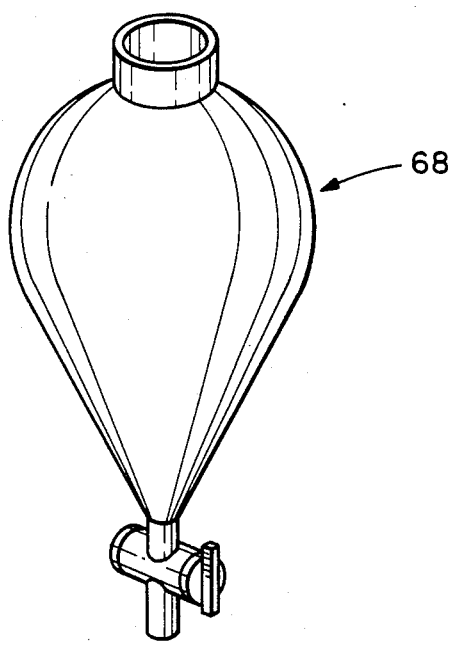
FIG. 6 is a perspective view of the components and their relationship for testing the product of the present invention.
Figure 6:
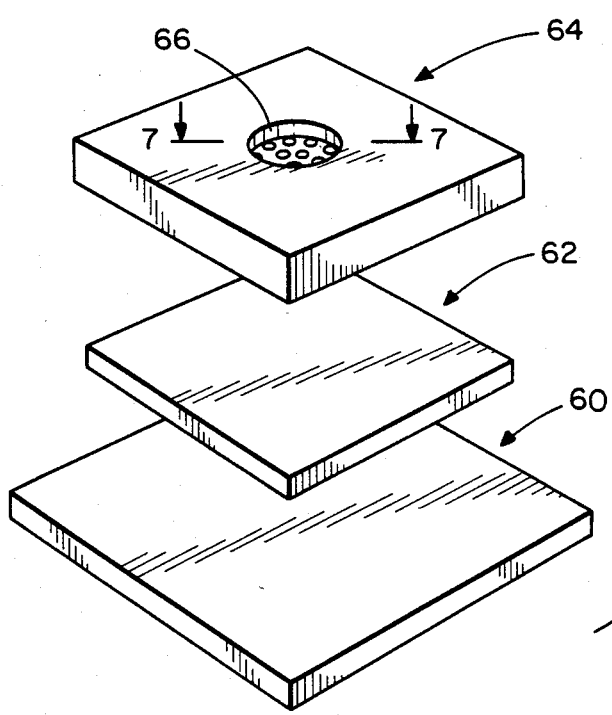
Figure 7:
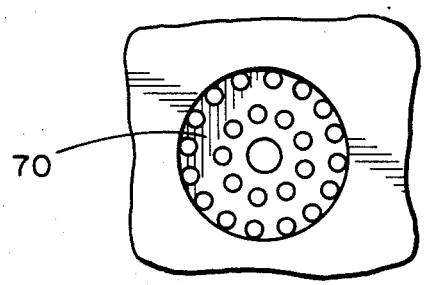
FIG. 7 is a top view of one portion of FIG. 6 taken along lines 7—7.
Figure 8:
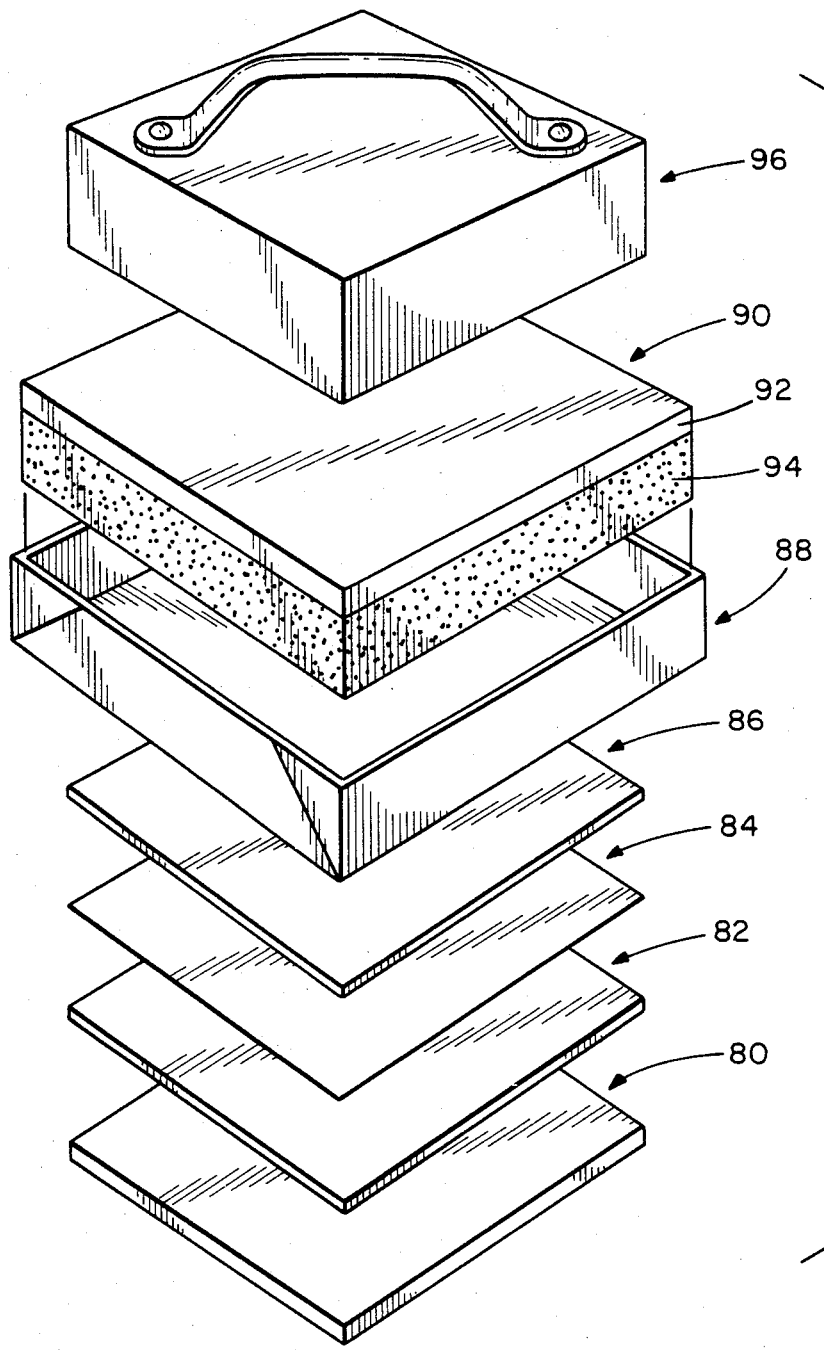
FIG. 8 is a perspective view of the components and their relationship for further testing the product of the present invention.

A test for dry fabric surface wetness is applied to all samples. FIGS. 6, 7 and 8 depict the apparatus used to perform the test. Referring to FIG. 6, an absorbent pad 62 approximately 4" square is placed on a plexiglass base plate 60 approximately 5" square. A strike-through plate 64 is placed on top of the absorbent pad. The strike-through plate 64 contains a cavity in its center.

The perforated plate at the base of cavity 66 is depicted in FIG. 7 as number 70. A separating funnel 68 is placed so that the funnel tip is one inch above the plexiglass plate 60. A predetermined portion of 1% saline solution is released into the cavity 66 and absorbed by the absorbent pad 62. The strike-through plate 64 is removed.

Referring now to FIG. 8, the absorbent pad 82 containing the solution is situated on top of the plexiglass base plate 80. A Five-inch square of the fabric 84 to be tested is placed on top of the wet absorbent pad 82. Next a pressure pad 90 is placed on top of the fabric 84. The pressure pad 90 consists of a square of lucite 92 affixed to a square of foam 94 covered by a polyethylene sheet 88. Lastly, a loading weight 96 is placed on the pressure pad 90. The total weight of the pressure pad 90 and the loading weight 96 is eight pounds.

The weights are left on the fabric sample for three minutes. After the three minutes, the weights are removed and the pressure pad 90 is wiped dry. A weighed square of filter paper 86 is placed on top of the fabric 84. The pressure pad and loading weight are then placed on top. The sample is allowed to equilibrate for 2.0 minutes. The filter paper is then removed and weighed.

The difference in weight of the wet and dry filter paper is reported as the dry surface wetness of the fabric. In Table 2, the figures below the 6x, 6.5x, 7x and 7.5x denote the dry surface wetness reported in grams when the amount of liquid added to the absorbent pad was six times the weight of the pad or 6.5 times the weight of the pad, etc. Approximately 6.8x is the saturation level for the absorbent pad. Samples A-C correspond to A-C in Table 1 and depict the present invention. Samples P-T correspond to the prior art samples set forth in Table 1.

TABLE 2

| Sample No. | Dry Fabric Surface Wetness in Grams | | | |
|---|---|---|---|---|
| | 6× | 6.5× | 7× | 7.5× |
| A | 0.079 | 0.084 | 0.76 | 4.0 |
| B | 0.076 | 0.075 | 0.35 | 3.81 |
| C | 0.063 | 0.061 | 0.14 | 2.06 |
| Prior Art | | | | |
| P | 2.47 | 2.84 | 3.37 | 3.65 |
| Q | 2.19 | 2.85 | 3.10 | 3.64 |
| R | 0.33 | 1.42 | 3.08 | 3.72 |
| S | 0.43 | 0.52 | 2.55 | 3.64 |
| T | 0.08 | 0.62 | 1.91 | 3.55 |

Table 2 above clearly shows that the fabric of the present invention resists strike back of liquid and thus is particularly suitable for use as a facing on a disposable diaper or the covering on an incontinent pad, a sanitary napkin, a tampon or the like. The machine direction tensile strengths for samples A-C range from 1.1 to 1.4 lbs. per inch of width and the cross direction tensile strengths range from about 0.7 to about 1.0 lbs. per inch of width.

The foregoing description and the drawings are illustrative and are not to be taken as limiting. Still other variations and modifications are possible without departing from the spirit and scope of the present invention.

We claim:

1. A disposable diaper comprising: a moisture-impervious backing sheet; an absorbent batt positioned in superposed relationship with respect to the backing sheet, the batt being smaller than the backing sheet and spaced inwardly from the longitudinal sides thereof; and a moisture pervious facing fabric positioned in superposed relationship with respect to the batt on the side opposite the backing sheet, the facing being larger than the batt and having longitudinal side margins thereof secured to the backing sheet, said facing fabric consisting essentially of a low density, resin-bonded, nonwoven fabric of resilient, synthetic, staple fibers selected from the group consisting of polyethylene, polyester, polypropylene, nylon and acrylic fibers and having a density less than about 0.06 gm/cc at 0.16 lb/sq. in. load, and a weight less than about 3 oz/sq. yd., said fabric during formation having been impregnated with a binder to provide a solution pickup of less than about 180 percent and a dry-solids-add-on from about 30 percent to about 50 percent.

2. The disposable diaper of claim 1 wherein the staple fibers are polyester fibers.

3. A sanitary napkin comprising: an absorbent core at least partially encompassed by a moisture impermeable barrier, said absorbent core and said barrier being wrapped by a cover, said cover consisting essentially of a low density, resin-bonded, nonwoven fabric of resilient, synthetic, staple fibers selected from the group consisting of polyethylene, polyester, polypropylene, nylon and acrylic fibers and having a density less than about 0.06 gm/cc at 0.16 lb/sq. in. load, and a weight less than about 3 oz/sq. yd., said fabric during formation having been impregnated with a binder to provide a solution pickup of less than about 180 percent and a dry-solids-add-on from about 30 percent to about 50 percent.

4. The disposable napkin of claim 3 wherein the staple fibers are polypropylene fibers.

5. A tampon comprising: an absorbent pad generally of rectangular shape superimposed on a nonwoven fabric of substantially the same shape and size to form a blank, the blank being formed into a tampon shape, said fabric consisting essentially of a low density, resin-bonded, nonwoven fabric of resilient, synthetic, staple fibers selected from the group consisting of polyethylene, polyester, polypropylene, nylon and acrylic fibers and having a density less than about 0.06 gm/cc at 0.16 lb/sq. in. load, and a weight less than about 3 oz/sq. yd., said fabric during formation having been impregnated with a binder to provide a solution pickup of less than about 180 percent and a dry-solids-add-on from about 30 percent to about 50 percent.

6. The tampon of claim 5 wherein the staple fibers are polyester fibers.

* * * * *